(12) United States Patent
Otsubo et al.

(10) Patent No.: US 8,221,376 B2
(45) Date of Patent: Jul. 17, 2012

(54) DISPOSABLE ABSORBENT ARTICLE

(75) Inventors: Toshifumi Otsubo, Kagawa-ken (JP);
Hiroki Yamamoto, Kagawa-ken (JP);
Tomoko Sugito, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 671 days.

(21) Appl. No.: 12/341,423

(22) Filed: Dec. 22, 2008

(65) Prior Publication Data

US 2009/0105677 A1    Apr. 23, 2009

Related U.S. Application Data

(62) Division of application No. 10/920,459, filed on Aug. 18, 2004, now abandoned.

(30) Foreign Application Priority Data

Aug. 19, 2003  (JP) ................................. 2003-207952
Jun. 1, 2004   (JP) ................................. 2004-163419

(51) Int. Cl.
*A61F 13/15*    (2006.01)
*A61F 13/20*    (2006.01)
(52) U.S. Cl. ............................................... 604/385.27
(58) Field of Classification Search ......... 604/385.24–385.29, 389–391
See application file for complete search history.

(56) References Cited

U.S. PATENT DOCUMENTS

| 4,968,313 | A | 11/1990 | Sabee |
| 5,069,678 | A | 12/1991 | Yamamoto et al. |
| 6,049,915 | A | 4/2000 | Malowaniec |
| 6,743,213 | B1 * | 6/2004 | Minato .......................... 604/390 |
| 2002/0095132 | A1 | 7/2002 | Ashton et al. |
| 2002/0111596 | A1 * | 8/2002 | Fletcher et al. ........... 604/385.03 |
| 2003/0023216 | A1 * | 1/2003 | Carlucci et al. ................ 604/375 |

FOREIGN PATENT DOCUMENTS

| EP | 0941728 A2 | 9/1999 |
| JP | 3096152 B2 | 8/2000 |
| WO | 0113843 A1 | 3/2001 |

* cited by examiner

*Primary Examiner* — Melanie Hand
(74) *Attorney, Agent, or Firm* — Lowe, Hauptman, Ham & Berner, LLP

(57) ABSTRACT

In a disposable absorbent article such as a disposable diaper including fastener elements by means of which front and rear waist regions are releasably connected with each other, the fastener elements are not affected by contraction of elastic members arranged in these waist regions. In this absorbent article, the front waist region and/or the rear waist region is or are divided into an elasticized intermediate zone provided with the elastic members and inelasticized transversely opposite side edge zones contigious to transversely opposite side edges of the intermediate zone. The fastener elements are provided in the transversely opposite side edge zones.

9 Claims, 9 Drawing Sheets

DISPOSABLE ABSORBENT ARTICLE

This is a Divisional Application of U.S. application Ser. No. 10/920,459, filed on Aug. 18, 2004, which is based on, and claims priority from, Japan Applications Number 2003-207952, filed Aug. 19, 2003 and 2004-163419, filed Jun. 1, 2004. The disclosures of all above applications are hereby incorporated by reference herein in their entirety.

BACKGROUND OF THE INVENTION

The present invention relates to a disposable absorbent article used for absorption and containment of body wastes and to a method of making the same. The invention particularly relates to a disposable absorbent article such as an open or pull-on type diaper for an infant or incontinent patient or training pants and a method of making the same. Regarding the method, the invention particularly to a method comprising the step of attaching waist-surrounding elastic members to a base sheet functioning to support an absorbent panel and to hold this in close contact with a wearer's body.

WO 01/13843 A1 (hereinafter referred to as "Citation 1") relating to an absorbent article such as a disposable diaper discloses a structure comprising a plurality of elastic members provided in a rear waist region of the article and fastener means detachably connecting the rear waist region with a front waist region of the article wherein the fastener means are fixed to the rear waist region so as to overlap the elastic members.

Japanese Patent No. 3096152 (hereinafter referred to as "Citation 2") relating to a disposable diaper discloses a structure comprising front and rear waist regions previously connected to each other so that the diaper may be selectively used as an open or pull-on type diaper, elastic members attached to front and rear waist regions, respectively, a pair of fastener means attached to transversely opposite side edge portions of the front waist region, respectively, another fastener means attached to the rear waist region so as to cooperate with those on the front waist region and a pair of tear off lines provided along the transversely opposite side edge portions of the front waist region, respectively, so that, if desired, the front waist region can be torn off from the rear waist region.

In the case of the absorbent article disclosed in Citation 1, the fastener means are fixed to the rear waist region so as to overlap the elastic members, so the fastener means are formed with gathers as the elastic members contracts. Such gathers make it difficult to bring the fastener means in a firm engagement with a landing zone and an unstable engagement is accompanied with a problem that the fastener means may be unintentionally disengaged from the landing zone.

As one of measures to overcome such a problem, it may be contemplated that none of the elastic members is distributed over the part of the waist region to be provided with the fastener means. While it is technically possible to provide the waist region partially with the elastic members, such a measure is not suitable for a mechanical apparatus driven at a high speed to mass produce the article as described herein at a low cost. For this reason, in generally, the elastic members are provided along a full length of a waist-surrounding circumference and the fastener means are attached to the waist region so as to overlap these elastic members.

In the case of the diaper disclosed in Citation 2, the front waist region is provided along its transversely opposite side edge portions with a pair of tear off lines, respectively, along which the front waist region are torn off from the rear waist region. Assumed that these waist regions are formed by a nonwoven fabric made of staple fibers or continuous filaments of synthetic resin as this is usually the case and particularly such a nonwoven fabric contains fibers or filaments oriented to cross the tear off direction defined by the tear off lines, it is difficult to tear the front waist region off from the rear waist region.

SUMMARY OF THE INVENTION

A disposable absorbent article includes an absorbent chassis having a first waist region, a second waist region, and a crotch region extending in a longitudinal direction of said chassis between said waist regions; first elastic elements provided in at least said first waist region and stretchable and contractible in a transverse direction of said chassis; second elastic elements provided along transversely opposite sides of said crotch region; and fasteners provided along transversely opposite side edge portions of the first waist region and releasably directly engageable, in use, with corresponding areas of the second waist region to releasably connect the first and second waist regions when the article is being worn by a wearer.

The first waist region includes an elasticized intermediate zone which is elasticized by the first elastic elements, and inelasticized transversely opposite side edge zones which are continuous to transversely opposite sides of said intermediate zone, respectively, and in which the fasteners are attached to the first waist region, the inelasticized side edge zones are free of absorbent material. The fasteners are attached to the first waist region in the transversely opposite side edge zones through the intermediary of respective reinforcing layers made of material provided separately of the first waist region.

The chassis includes a laminate of at least two sheets intermittently bonded together, a first sheet of said at least two sheets extends continuously without interruption in the first waist region and in the transverse direction from one of the inelasticized side edge zones into the elasticized intermediate zone and then into the other of the inelasticized side edge zones, and defines the transversely opposite side edge portions of said first waist region. The fasteners are bonded to the first sheet along the transversely opposite side edge portions of the first waist region, and the first elastic elements are interposed between the two sheets.

The article further includes two ear flaps having a tensile strength at least equal to and a stiffness higher than the laminate of said chassis, wherein said ear flaps are permanently joined to transversely opposite sides of said chassis in the second waist region; the ear flaps defining thereon the corresponding areas releasably engageable with the respective fasteners attached to the first waist region.

Each of the first elastic elements has an intermediate segment in the elasticized intermediate zone, and at least one side segment in each of the inelasticized transversely opposite side edge zones, the at least one side segment being severed from the intermediate segment and whereby elasticity of the intermediate zone does not affect the inelasticized transversely opposite side edge zones.

DETAILED DESCRIPTION OF THE PREFERRED EMBODIMENTS

Figure 1:
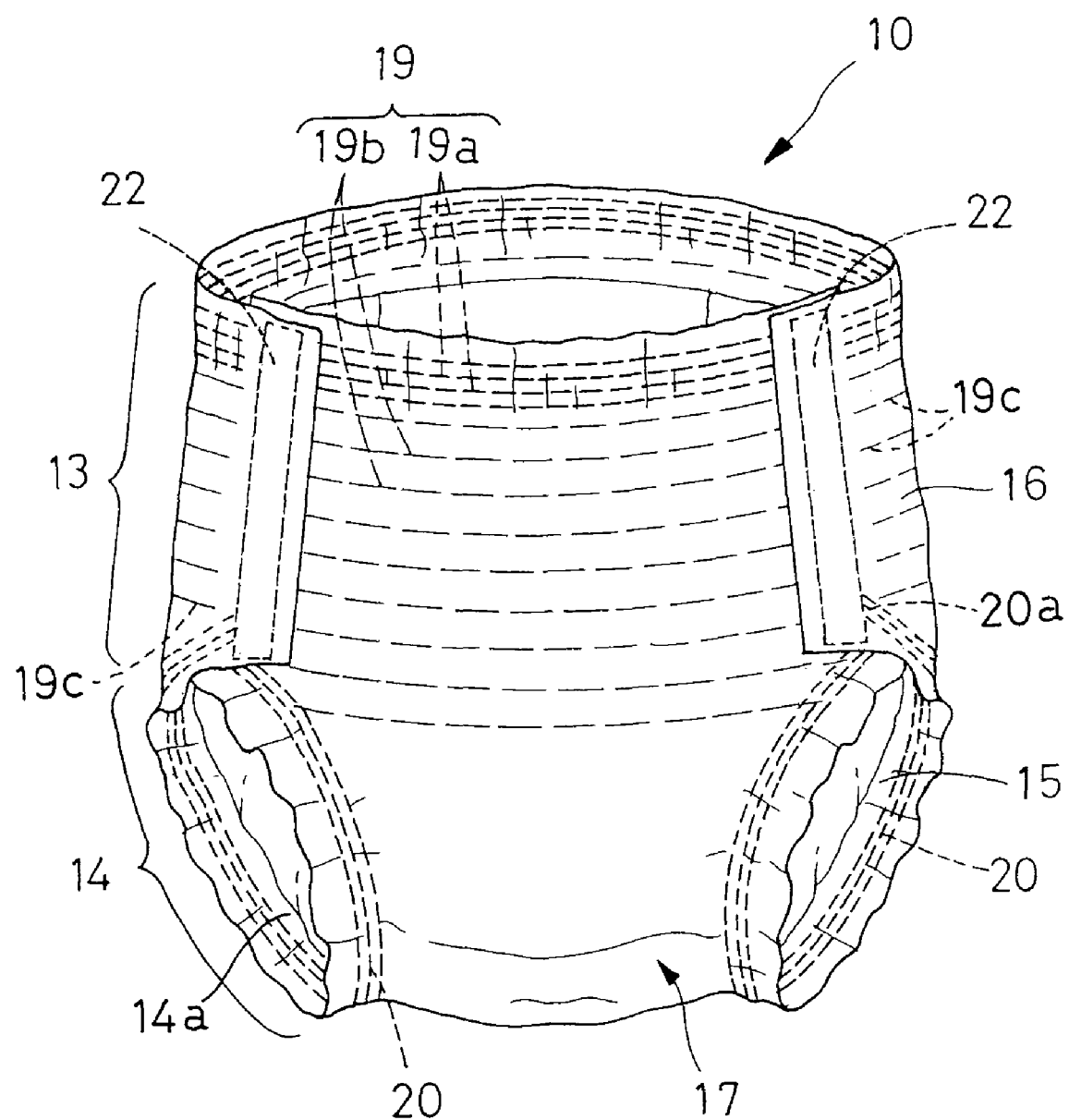
FIG. 1 is a perspective view showing a disposable diaper according to a first embodiment of the invention having front and rear waist regions connected to each other.
Figure 2:
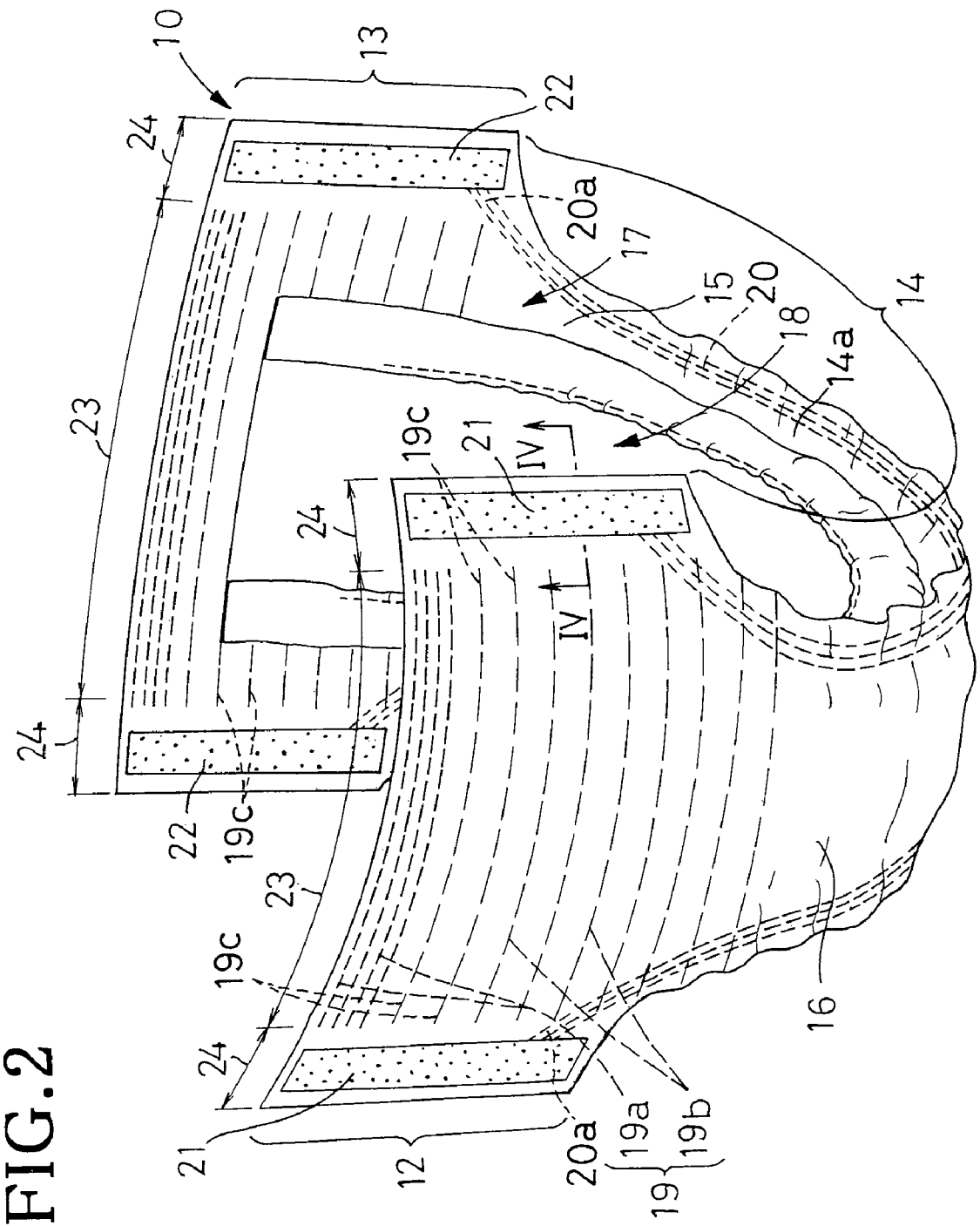
FIG. 2 is a perspective view showing the diaper of FIG. 1 having the front and rear waist regions disconnected from each other.
Figure 3:
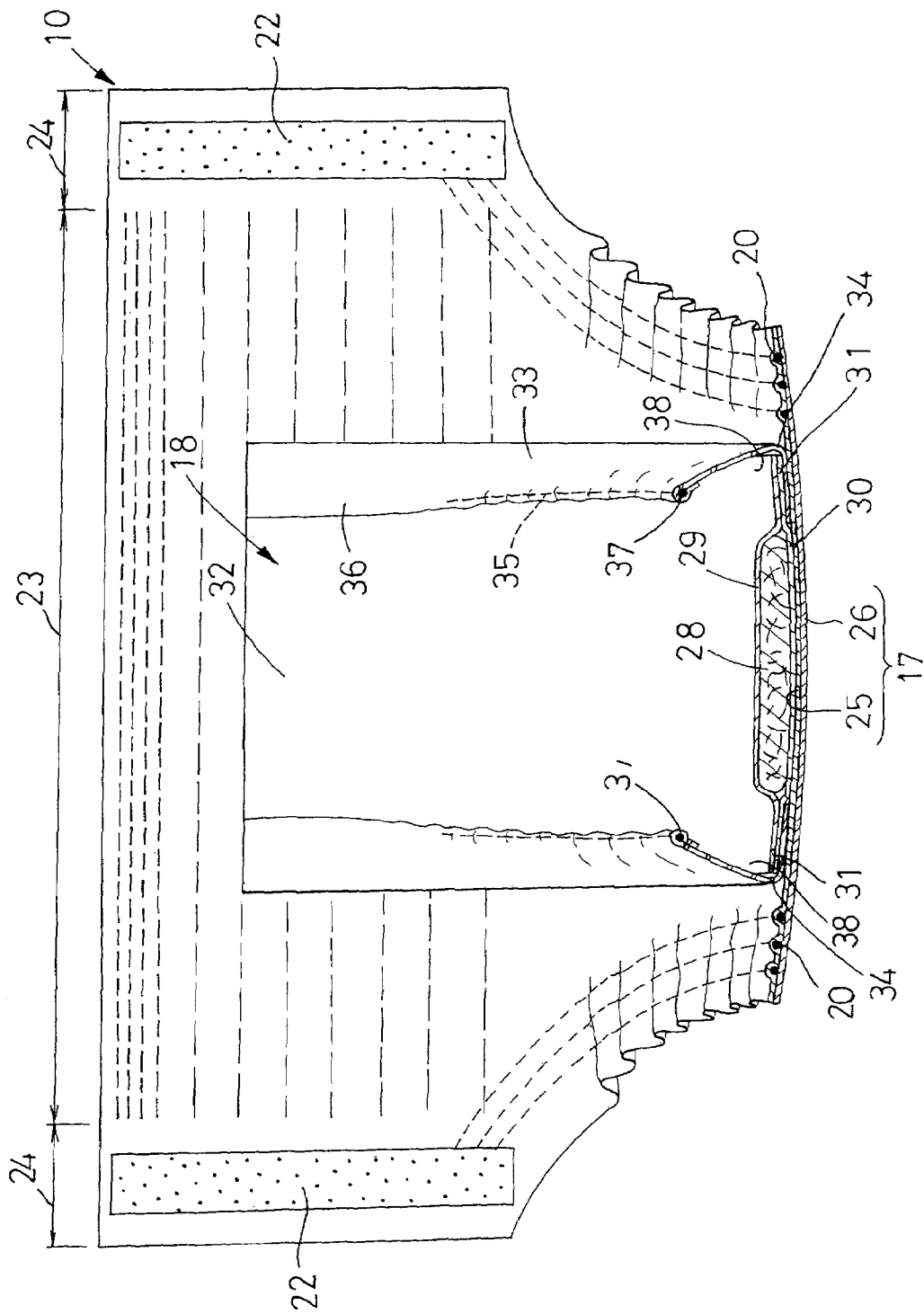
FIG. 3 is a sectional view showing the diaper of FIG. 1 as taken along a transverse center line bisecting a longitudinal dimension of the diaper.
Figure 4:
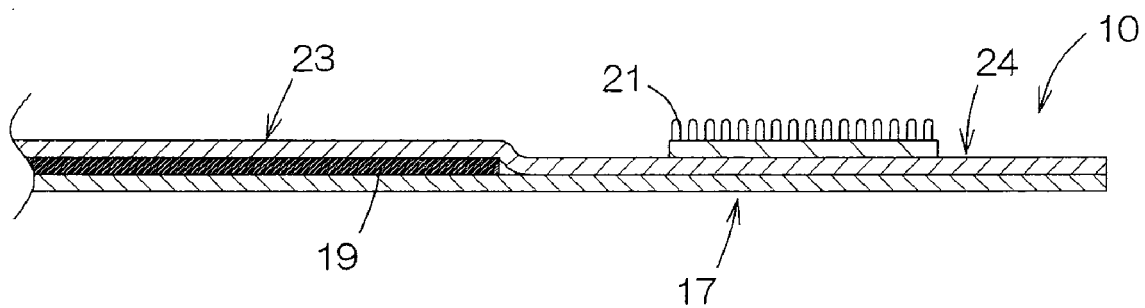
FIG. 4 is a sectional view taken along the line IV-IV in FIG. 2.

A disposable diaper illustrated in FIGS. 1 through 3 as a specific embodiment of the disposable absorbent article according to the invention has an absorbent chassis 10 comprising a front waist region 12, a rear waist region 13, a crotch region 14 extending between these waist regions 12, 13, and a pair of leg regions 14a defined by transversely opposite side edge portions of the crotch region 14. The chassis 10 comprises a base sheet 17 and an absorbent structure 18. The base sheet 17 has inner and outer surfaces 15, 16 and exhibits a relatively high flexibility and liquid-resistance and the absorbent structure 18 extends over the crotch region 14 further into the front and rear waist regions 12, 13. The chassis 10 further comprises a plurality of elastic members 19 arranged in the front and rear waist regions 12, 13 as first elastic members, a plurality of elastic members 20 provided in the crotch region 14 along the respective leg regions 14a as second elastic members, and fastener means 21, 22 attached to the outer surface 15 of the base sheet along the transversely opposite side edge portions of the front waist region 12 and attached to the inner surface 15 of the base sheet 17 along the transversely opposite side edge portions of the rear waist region 13, respectively, so that the fastener means 21, 22 may be releasably engaged with each other. In each of the front and rear waist regions 12, 13, an elasticized intermediate zone 23 containing the elastic members 19 arranged therein and inelasticized transversely opposite side edge zones 24 containing none of the elastic members 19 arranged therein are respectively defined (See FIG. 4). In the case of such diaper according to the invention basically arranged in this manner, the front and rear waist regions may be connected with each other by mutual engagement of the fastener means 21, 22 when the diaper is put on a wearer's body. While the invention has been described above on the basis of the open type diaper as a specific embodiment, the structural features of this embodiment are applicable to a pull-on type diaper as will be described later as a third embodiment of the invention.

The base sheet 17 is formed from a laminate composed of two hydrophobic fibrous nonwoven fabric sheets 25, 26 intermittently bonded together and curving inward in the crotch region 14 so as to have its width reduced. Thus the base sheet 17 as a whole has an hourglass-like planar shape. The nonwoven fabric sheets 25, 26 may be treated with repellent conventionally used for component materials constituting the article of the type as described herein if it is desired to enhance a liquid-resistant effect. These nonwoven fabric sheets 25, 26 may be selected from those obtained by the methods of well known art for making various fibrous nonwoven fabric sheets and the component fibers of these nonwoven fabric sheets 25, 26 also may be selected from those conventionally used as the component fibers for the article of this type.

The elastic members 19, 20 are fixedly interposed between the nonwoven fabric sheets 25, 26 of the base sheet 17 and extend in a transverse direction. Though not illustrated, fixation of the elastic members 19, 20 is preferably achieved by hot melt adhesive intermittently applied in a spiral pattern, dotted pattern, or linear or curved stripe-pattern. Material for these elastic members 19, 20 may be natural or synthetic material so far as the material has a rubber elasticity.

The elastic members 19 are arranged over almost whole area defined between the vicinity of respective upper edges of the front and rear waist regions 12, 13 and the vicinity of respective upper edges of the crotch region 14 as viewed in FIGS. 1 and 2. The elastic members 19a extending along an upper edge portion of a waist-hole are spaced apart one from another by a relatively small dimension and the elastic members 19b laid below the elastic members 19a are spaced apart one from another by a relatively large dimension. Alternatively, it is also possible to arrange both the elastic members 19a and the elastic members 19b so as to be spaced apart one from another by a uniform dimension, though no shown. While a tensile stresses of these elastic members 19a, 19b may be appropriately set zone by each of zones in which these elastic members 19a, 19b are arranged, depending on a particular purpose for which the article is used, these tensile stresses are set, in general, so that the elastic members 19a arranged in the vicinity of the waist-hole present a relatively high tensile stress and the elastic members 19b arranged in the remaining zone present a relatively low tensile stress. This is for the reason that the elastic members 19a should function to hold the article on the wearer's body while the elastic members 19b should function as an auxiliary means to ensure a good fit of the article around the wearer's body. To ensure such functions, these elastic members are fixed preferably at least longitudinally opposite end portions thereof to the base sheet 17. In this way, the base sheet 17 is not formed with gathers as these elastic members contract and an external appearance is protected from being disordered.

The elastic members 19, 20 respectively have longitudinally opposite end portions 19c, 20a preferably laid in the vicinity of the inner side edges of the respective fastener means 21, 22 and oriented so as to cross these side edges. The elastic members 19, 20 arranged in this manner are operatively associated or cooperate with each other through the intermediary of the fastener means 21, 22. Specifically, the contraction stress of the elastic members 19 is operatively associated with the contraction stress of the elastic members 20. Thus if the front and rear waist regions 12, 13 are elastically pressed against the wearer's waist with an appropriate fit, the leg regions of the diaper will be also elastically pressed against the wearer's legs correspondingly with an appropriate fit.

The fastener means 21, 22 function substantially in the same manner as those of well known under the trademark "Velcro" or "Magic Tape". One of the fastener means 21, 22 comprises a hook member consisting of a hook-backing and a plurality of hooks protruding from one surface of the hook backing and the other of the fastener means 21, 22 adapted to be engaged with this hook member comprises a loop member consisting of a loop backing and a plurality of loops protruding or rising up out from one surface of the look backing.

These fastener means 21, 22 are made of material having a stiffness higher than the base sheet 17. These fastener means 21, 22 may be replaced by pressure-sensitive adhesive applied directly or indirectly and continuously or intermittently on the chassis 10. As used herein the term "applied indirectly on the chassis" means that an appropriate backing is coated with adhesive and this backing is bonded to the chassis 10 to form a fastener. The fastener means comprising the loop member may be eliminated so far as the fibrous nonwoven fabric or the reticular fabric constituting the article can function as the loop member. The fastener means 21, 22 may be fixed to the front and rear waist regions 12, 13 along the transversely opposite side edge zones thereof using hot melt adhesive and/or welding technique. Though not illustrated, such fixation is preferably made through the intermediary of a reinforcing layer 45 as will be described later with respect to a third embodiment of the invention.

The pressure-sensitive adhesive may be selected from those conventionally used in the technical field of this invention, for example, natural rubber-based adhesive or synthetic rubber-based adhesive such as acryl-based, silicone-based, or urethane-based adhesive. It is also possible to use, as the pressure-sensitive adhesive, natural latex mixed with one or more selected from the group consisting of SBR emulsion, IR emulsion, acrylic polymer, vinyl acetate, and ethylene/vinyl acetate copolymer in a given proportion. A coating thickness of the adhesive is in a range of approximately 5 to 100 µm, preferably in a range of approximately 10 to 60 µm.

In view of desired advantageous effect as will be described, the fastener means 21, 22 preferably have tape-like shapes and continuously extend in a longitudinal direction of the chassis 10 over ranges substantially defined between longitudinally opposite ends of the front and rear waist regions 12, 13, respectively. Specifically, when the rear waist region 13 or the front waist region 21 are stretched by the wearer's parent or care personnel with the transversely opposite side edge portions of this waist region held by the hands in order to put the article on the wearer's body, a tensile force for such stretching can be exerted on practically whole area of this waist region. Consequently, there occurs no anxiety that this waist region might be evenly or unevenly formed with gathers and prevented from coming in close and neat contact with the wearer's body. In addition, an area of engagement as wide as possible can be ensured and thereby an engagement strength can be enhanced. Furthermore, the fastener means 21, 22 have a stiffness sufficient to maintain the shapes of the front and rear waist regions 12, 13. Therefore the fastener means 21, 22 can be easily put in mutual engagement and disengagement. Though not illustrated, an alternative arrangement is also possible according to which the fastener means 21, 22 intermittently extend in the longitudinal direction of the article or a plurality of the fastener means 21, 22 extend in parallel one to another along each of the transversely opposite side edges so far as the effect as has been described a just above is achieved.

Depending on a particular size of the diaper, each of the fastener means 21, 22 in the illustrated embodiment may have a width dimension in a range of about 2 mm to about 30 mm and a length dimension in a range of about 50 mm to about 200 mm, preferably a width dimension in a range of about 5 mm to about 20 mm and a length dimension in a range of about 50 mm to about 150 mm. Such dimensioning is effective to assure a sufficient peeling and shearing strength required for the fastener means 21, 22 particularly when these fastener means comprise the adhesive applied directly or indirectly on the chassis 10.

As will be best seen in FIG. 3, the absorbent structure 18 comprises a liquid-absorbent core 28, a flexible and liquid-pervious upper sheet 29 covering a top surface of the core 28 and a flexible and liquid-resistant lower sheet 30 covering a bottom surface of the core 28. The upper and lower sheets 29, 30 respectively have portions 31, 32 extending outward beyond a peripheral edge of the core 28 and bonded together. The absorbent structure 18 is provided along its transversely opposite side edges with a pair of flaps 33 having a relatively high flexibility, contractility and liquid-resistance. Each of the flaps 33 has a proximal edge portion 34 fixed between the base sheet 17 and the portion 31, a distal edge portion 35 and longitudinally opposite end portions 36 which are folded inward and bonded in such a folded state to the upper sheet 29. Each of the flaps 33 further has an elastic member 37 attached in a stretched state to the distal edge portion 35 so that the elastic member 37 may function as an elastic spacer means to space apart the flap 33 upward from the upper sheet 29 thereby forming a channel 38 adapted to receive body waste.

The core 28 comprises a mixture of fluff pulp and water-insoluble polymer particles having an absorption capacity corresponding to at least 20 times of its own weight, both components being well known in the art and appropriately compressed. Compared to the upper and lower sheets 29, 30 having a high flexibility, the core 28 is relatively stiff, i.e., semirigid. Though not illustrated, a general entirety of the core 28 is preferably wrapped with a liquid-absorbent/diffusible sheet such as tissue paper not only to achieve convenience for production of the article but also to prevent the core 28 from getting out of its initial shape and to prevent the polymer particles from falling off.

The upper and lower sheets 29, 30 are formed from nonwoven sheets. Such nonwoven sheets may be selected from those obtained by various methods of well known art for making a fibrous nonwoven fabric and conventionally used as the component material for the article of the type described herein.

To simplify the description of a second embodiment, the components and portions corresponding to those in the first embodiment will be denoted by the same reference numeral as those used to illustrate the first embodiment and the arrangements similar to those in the first embodiment will be omitted wherever possible.

Figure 5:
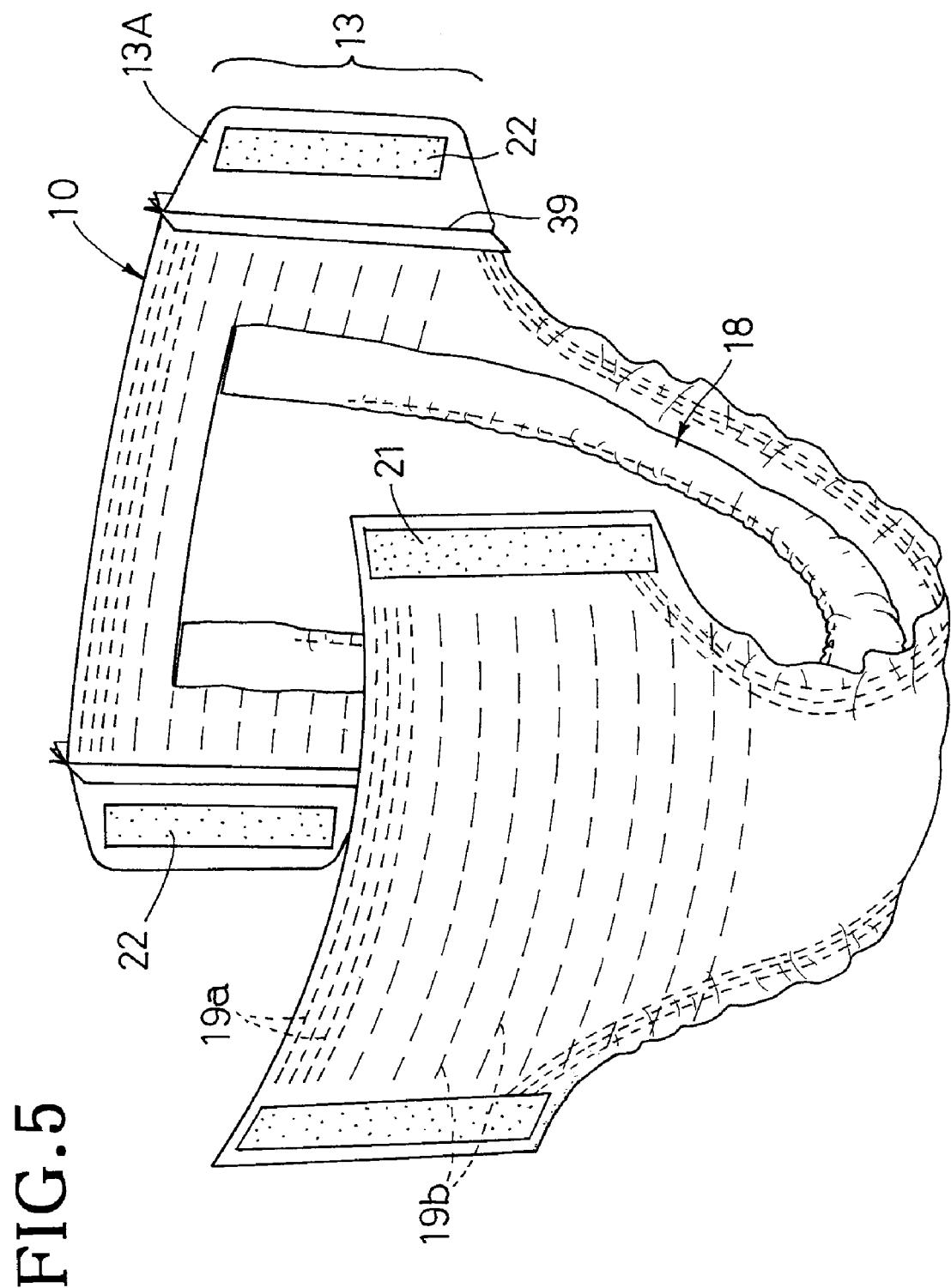
FIG. 5 is a perspective view showing a disposable diaper according to a second embodiment of the invention having front and rear waist regions disconnected from each other.

FIG. 5 shows the second embodiment distinguished from the first embodiment only with respect to the transversely opposite side edge portions of the rear waist region 13. More specifically, ear flaps 13A made of separately prepared material are connected to the transversely opposite side edge portions of the rear waist region 13 so as to form a part of the chassis 10 according to the second embodiment while ear portions on the transversely opposite side edge portions of the rear waist region 13 are integrally formed by the chassis 10 according to the first embodiment. The ear flaps 13A are formed from a sheet material such as a fibrous nonwoven fabric having a tensile strength at least equal to the tensile strength of the base sheet 17 and preferably having a stiffness higher than the stiffness of the respective sheet materials constituting the base sheet 17. The respective ear flaps 13A are connected to the chassis 10 along seaming lines 39 by heat-sealing or sonic-sealing proximal edge portions of the respective ear flaps 13A and the respective side edge portions of the chassis 10 with each other. The ear flaps 13A are provided on the inner surfaces thereof with the fastener means 22.

Figure 6:
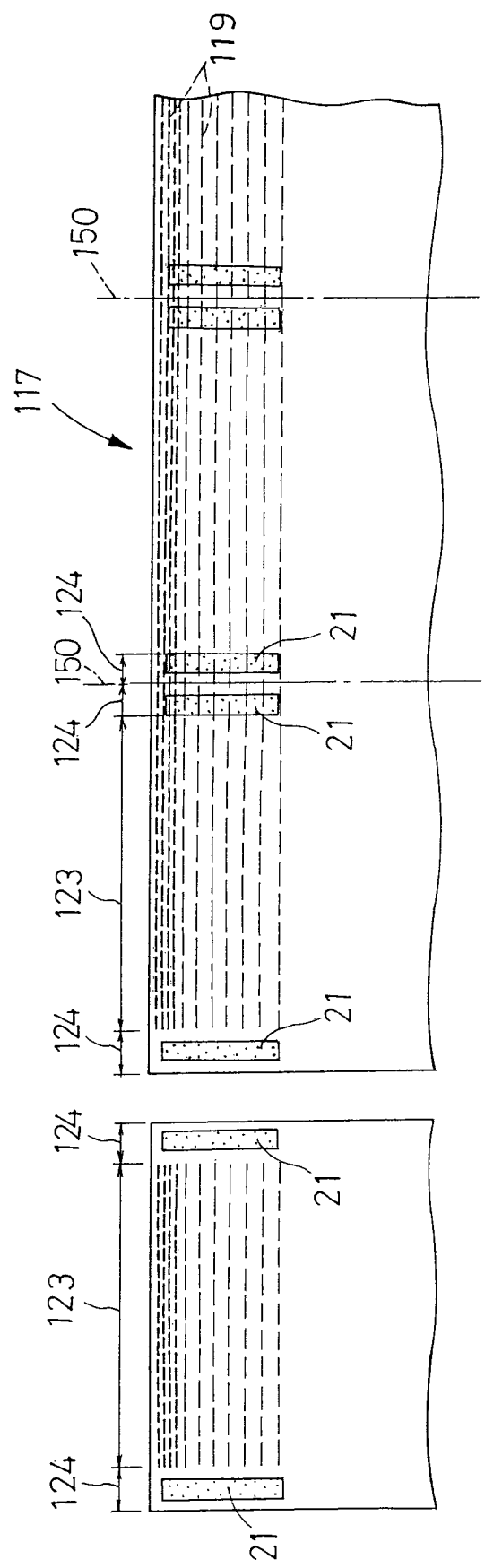
FIG. 6 is a plan view partially illustrating a process for making the diapers according to the first and second embodiments of the invention.

FIG. 6 schematically illustrates a method for attaching the elastic members 19 to one of the front and rear waist regions 12, 13. Referring to FIG. 6, a continuous web 117 includes regions corresponding to a series of the front waist regions 12 or the rear waist regions 13 but remaining regions corresponding to a series of the other waist regions, the absorbent structure 18 and the leg-surrounding elastic members 20 are not illustrated.

According to this method, a plurality of continuous elastic members 119 spaced apart one from another and extending in parallel one with another, all being stretched at a given ratio are fed onto the continuous web 117 destined to define the base sheets 17. First zones 123 of the web 117 destined to define the intermediate zones 23 are coated with hot melt adhesive (not shown) while second zones 124 destined to define the transversely opposite side edge zones 24 are not coated with the adhesive. The elastic members 119 are bonded to the first zones 123 by means of the adhesive coated thereon. In the respective second zones 124, mechanical fasteners are attached to the web 117 or pressure-sensitive adhesive is directly or indirectly applied on the chassis 10 to form the fasteners. Along a boundary line 150 between each pair of the adjacent second zones 124, the web 117 is cut together with the elastic members 119. Thereupon, as will be seen on the left side of the diagram, each group of the elastic members 119 laid in the respective second zones 124 automatically contract or snap back.

For high speed mass production of the article, the step of cutting is preferably carried out after the individual components have assembled in the form of the continuous web comprising the individual articles arranged side by side.

In this embodiment, to simplify the description, the components and portions corresponding to those in the first embodiment will be denoted by the same reference numeral as those used to illustrate the first embodiment and the arrangements similar to those in the first embodiment will be omitted wherever possible.

Figure 7:
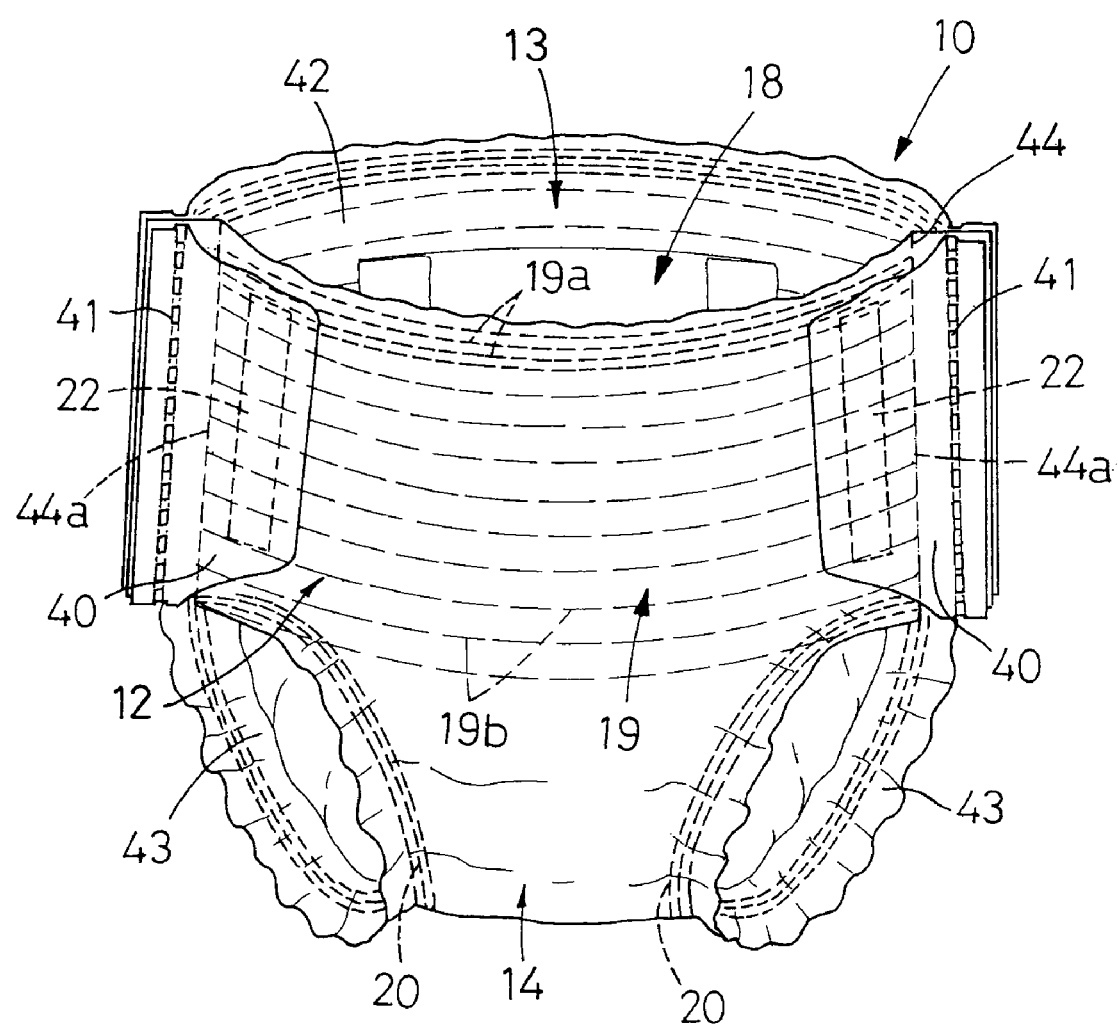
FIG. 7 is a perspective view showing a disposable diaper according to a third embodiment of the invention having front and rear waist regions connected to each other.
Figure 8:
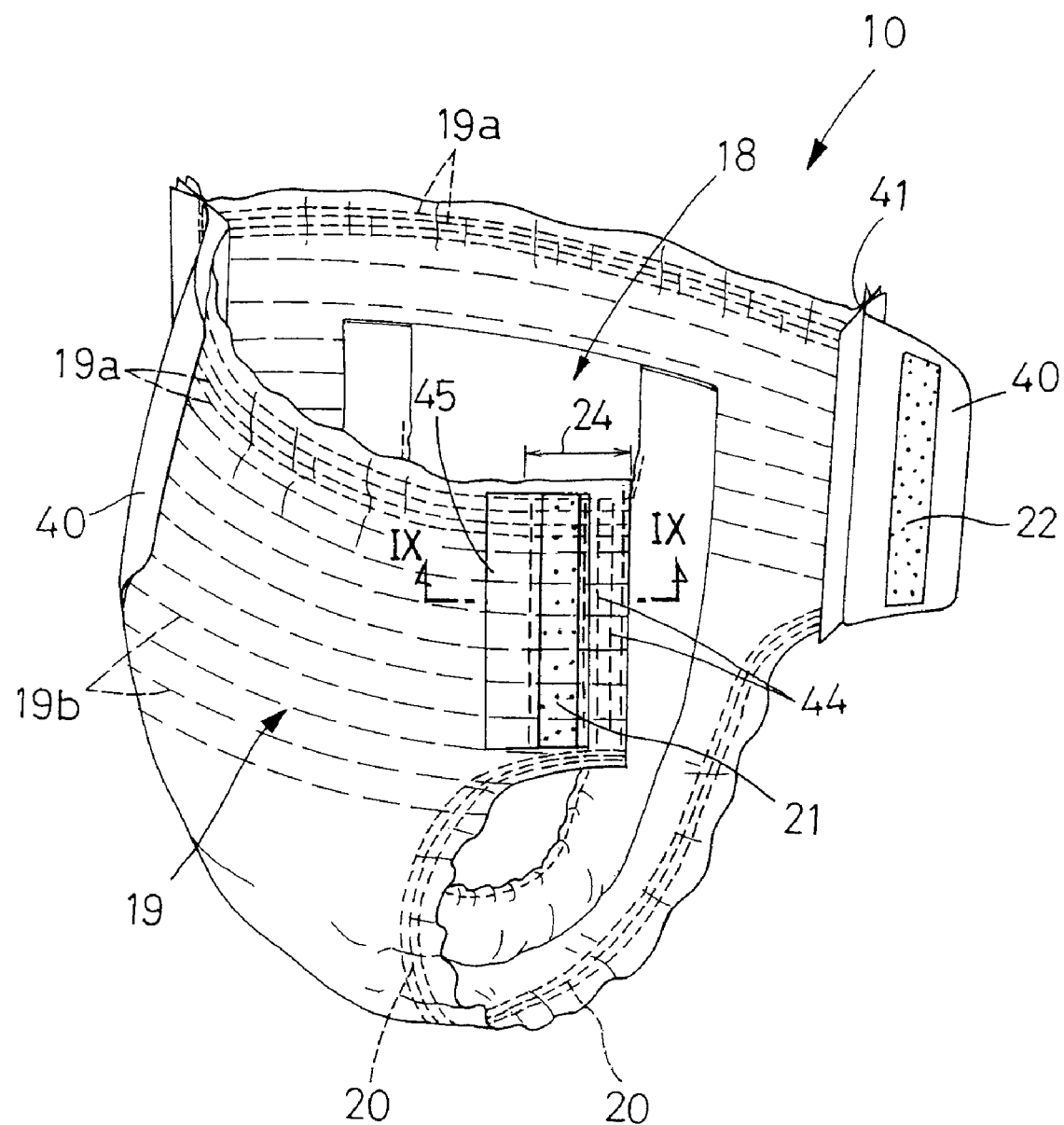
FIG. 8 is a perspective view showing the diaper of FIG. 7 having the front and rear waist regions partially disconnected from each other.
Figure 9:
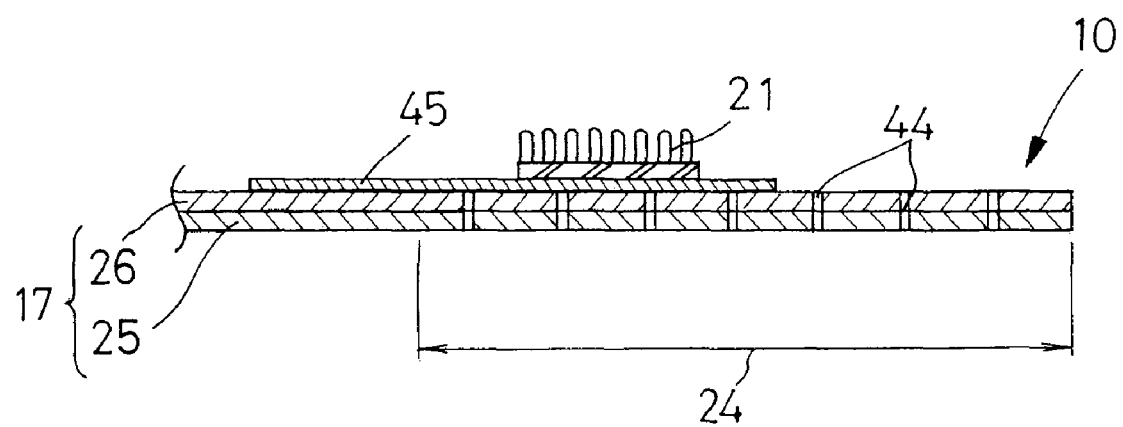
FIG. 9 is a sectional view taken along the line IX-IX in FIG. 8.

As will be apparent from FIGS. 7 through 8, the front and rear waist regions 12, 13 of the absorbent chassis 10 and the side edge portions of the respective ear flaps 40 are overlapped and connected together by seam lines 41 extending along these side edge portions, whereupon a pull-on type diaper is formed with a waist-hole 42 and a pair of leg-holes 43.

In the front waist region 12, the elastic members 19 extend beyond the intermediate zone 23 to the transversely opposite side edge zones 24 and these extensions of the elastic members 19 are cut into small segments in the longitudinal direction thereof through the base sheet 17 by a plurality of rows of slits 44 each extending intermittently in the vertical direction of the article and arranged in parallel one to another in the transverse direction of the article. In consequence, these segments of the elastic members in the transversely opposite side edge zones 24 have no more contractility. In general, the step of cutting the elastic members 19 is mechanically achieved in a mechanical using a sharp cutter. Alternatively, the step of such cutting may be carried out using ultrasonic waves emitted from an ultrasonic wave apparatus comprising an anvil and a horn. The ultrasonic wave treatment allows the elastic members to be cut or deteriorated without cutting the base sheet 17. An equivalent effect may be obtained by coating the target regions of the base sheet 17 with hot melt adhesive and hardening the adhesive to make these target regions stiff.

The slits 44 function not only to deprive the elastic members 19 of contractility thereof but also to facilitate the front waist region 12 to be torn off from the rear waist region 13. Particularly in order to facilitate the front waist region 12 to be torn off from the rear waist region 13, at least the row of slits 44a adjacent the seam line 41 preferably extends from the upper edge to the lower edge of the front waist region 12. Each of the reinforcing layers 45 has a sufficiently large contour size to cover a generally inner half of the side edge zone 24 on the outer surface of the front waist region 12 and the side edge portion of the intermediate zone 24. The fastener means 21 are permanently bonded to these reinforcing layers 45 in the vicinity of the transversely opposite side edge zones 24 of the front waist region 12.

The ear flaps 40 are formed from a sheet material such as a fibrous nonwoven fabric having a tensile strength at least equal to the tensile strength of the base sheet 17 and preferably having a stiffness higher than the stiffness of the respective sheet materials constituting the base sheet 17. Unlike the embodiment as illustrated, it is also possible to form these ear flaps 40 integrally with the rear waist region 13 from the same material as that of the rear waist region 13.

The reinforcing layer 45 may be formed by bonding a sheet material having an appropriate strength and stiffness such as a fibrous nonwoven sheet or plastic film to the base sheet 17 using hot melt adhesive or welding technique such as heat- or sonic-sealing. Alternatively, the base sheet 17 may be coated with hot melt adhesive and this hot melt adhesive may be hardened to form the reinforcing layer 45. In the latter case, hot melt adhesive is preferably applied on the inner surface of the nonwoven sheet 25 constituting the base sheet 17. These reinforcing layers 45 reinforce at least partially the regions in which the fastener means 21 are laid as well as the regions in which the slits 44 are formed and thereby effectively prevent the fastener means from being deformed and prevent the slit-formed regions from being broken. In this way, these reinforcing layers 45 stabilize the engagement between the fastener means 21, 22.

While the process for making the article according to the third embodiment of the invention including the step of depriving the elastic members 19 of contractility in the transversely opposite side edge zones 24 is not illustrated, the process for making the article according to the first embodiment of the invention may be utilized except the formation of the slits 44 and attachment of the reinforcing layers 45. The process for making the third embodiment will be readily understood from the description given hereinabove of the article, so description of the process for making the third embodiment is eliminated here.

The article according to this embodiment can be easily converted to the open type diaper, if desired, merely by tearing the front waist region 12 off from the rear waist region 13 along the slits 44a serving as tear off guide.

Deprivation of the elastic members 19 of contractility by the slits 44 as well as the formation of the reinforcing layers 45 may be adopted in the first and second embodiments. Furthermore, the features of the first, second and third embodiments may be appropriately combined to obtain an alternative embodiment not illustrated.

One or more of the embodiments provide a disposable absorbent article adapted to solve one or more problems as has been described above and a method of making the same.

One or more of the embodiments provide a disposable absorbent article including a fastener means adapted to be free from the affection of elastic members even when these elastic members contract and a method of making the same.

One or more of the embodiments provide a disposable absorbent article having front and rear waist regions previously connected with each other and adapted to be easily torn off from one another, if desired, and a method of making the same.

As used herein, the term "chassis" refers to a main body of an absorbent article. Namely, the chassis is formed from a material differing from the material for the main body in the conventional disposable absorbent article and components such as tape-like tabs attached to transversely opposite side edge portions of the main body so as to extend outward from these side edge portions do not correspond to the transversely opposite side edge portions of the chassis according to the present invention. The fastener means do not include a fastener means provided on such tabs.

As used herein, the term "elasticized" refers to a state that elastic members have been provided in desired regions made of a material having no rubber elasticity and thereby such regions have been imparted with elastic contractility.

As used herein, the term "inelasticized" refers to a state that the elastic members were provided in desired regions but subsequent treatment has made these regions as if none of the elastic members are present in these regions or refers to a state that, even though the elastic member are present in those regions, the elastic members in the relevant regions have been deprived of contractility required for the article by subsequent treatment.

As used herein, the term "fastener means" refers to a means having function substantially the same as those well known in the name of Velcro (trademark) or Magic Tape (trademark). Specifically, the term "fastener means" refers to the means comprising a hook member consisting of a hook backing and a plurality of hook elements extending upward from the hook backing and a loop member consisting of a loop backing and a plurality of loop elements projecting or standing out from the loop backing so that these hook and loop members may be releasably engaged with each other. It should be noted here that the material having a loop function such as a fibrous nonwoven fabric constituting the article may be used as the loop member. It is also possible to replace the hook member and the loop member by an adhesive applied directly or indirectly on the chassis as "fastener means".

As used herein, the term "first waist region" refers to one of the front and rear waist regions of the article and the term "second waist region" refers to the other of the front and rear waist regions.

In accordance with one or more embodiments, the first waist region has an elasticized intermediate zone and inelasticized transversely opposite side edge zones in which the fastener means are attached to the first waist region.

In accordance with one or more embodiments, the first and/or second waist region(s) is or are divided into the elasticized intermediate zone and inelasticized transversely opposite side edge zones in which the fastener means are provided. Such a unique arrangement is effective to protect the fastener means from undulation due to contraction of the elastic members laid to elasticize at least the waist regions and, in consequence, proper engagement between the cooperating fastener means is assured. In this way, there is no anxiety that the fastener means might be affected or deteriorated by contraction of the elastic members and unintentionally disengaged from each other as has been described above in the paragraph regarding the prior art.

In accordance with one or more embodiments, the fastener means are attached to the first waist region in the transversely opposite side edge zones preferably through the intermediary of reinforcing layers made of material provided separately of the first waist region. The reinforcing layers are effective to avoid undesirable deformation and breakage of zones in the fastener means are located and to stabilize mutual engagement of these fastener means.

In accordance with one or more embodiments, the chassis comprises a flexible and liquid-resistant base sheet having inner and outer surfaces and a semirigid absorbent panel fixed to the inner surface. Such an arrangement is effective to enhance a good fit to the wearer's body, to prevent body waste from leaking, to protect the wearer from experiencing a feeling of discomfort due to stiffness of the article and to prevent the chassis and the absorbent panel from unintentionally moving relatively to each other.

In accordance with one or more embodiments, the base sheet comprises a laminate sheet composed of at least two sheets intermittently bonded together and the first and second elastic means are interposed between said two sheets. Such an arrangement is effective to ensure a tensile and tear strength required for the base sheet and to reliably fix the elastic members to the base sheet.

In accordance with one or more embodiments, the first elastic means are provided substantially over a whole area of the intermediate zone and the first and second elastic means comprise a plurality of thread- or strand-like means having rubber elasticity. Such an arrangement is effective to hold the first and second waist regions around the wearer's waist over a relatively wide range without giving the wearer oppressive feeling.

In accordance with one or more embodiments, the fastener means comprise a mechanical fasteners or adhesive fastener directly or indirectly applied on the chassis in desired regions thereof and are continuously or intermittently provided on the first waist region over a range defined between end portions opposed in a vertical direction of the chassis. Such an arrangement is effective, particularly when the article has a structure by which the first and second waist regions are detachably connected with each other, to ensure that a tensile force with which the wearer's parent or care personnel pulls the first and/or second waist region(s) with the transversely opposite side edge portions thereof held in the hands can be transmitted to a generally whole area of the waist region(s), to facilitate the wearer's parent or care personnel to put the article on the wearer's body, to assure a wide area of engagement and thereby to improve a strength of engagement.

In accordance with one or more embodiments, the first and second elastic means comprise a plurality of elastic members and longitudinally opposite ends of the elastic members are laid in the vicinity of side edges of the fastener means and oriented so as to cross these side edges. Such an arrangement allows the first and second elastic members to be operatively associated or to cooperate with each other. Specifically, a contraction stress of the first elastic members are operatively associated with a contraction stress of the second elastic members. In other words, if the waist regions are elastically pressed against the wearer's waist at an appropriate pressure, the leg regions also will be elastically pressed against the wearer's legs at an appropriate pressure. Even when a pressure at which the article is elastically pressed against the wearer's body must be adjusted, it will be unnecessary to adjust the pressure at which the waist regions should be pressed against the wearer's waist and the pressure at which the leg region should be pressed against the wearer's legs.

The article is an open type diaper or a pull-on type diaper.

What is claimed is:
1. A disposable absorbent article, comprising:
an absorbent chassis having a first waist region, a second waist region, and a crotch region extending in a longitudinal direction of said chassis between said waist regions;
first elastic elements provided in at least said first waist region and stretchable and contractible in a transverse direction of said chassis;
second elastic elements provided along transversely opposite sides of said crotch region; and fasteners provided along transversely opposite side edge portions of said first waist region and releasably engageable with corresponding areas of said second waist region to releasably connect said first and second waist regions;

wherein said first waist region comprises: an elasticized intermediate zone which is elasticized by the first elastic elements, and inelasticized transversely opposite side edge zones which are continuous to transversely opposite sides of said intermediate zone, respectively, said fasteners are attached to said first waist region, said inelasticized side edge zones are free of absorbent material;

wherein each of the first elastic elements comprises
- an intermediate segment in the elasticized intermediate zone, and
- at least one side segment in each of the inelasticized transversely opposite side edge zones, the at least one side segment being severed from the intermediate segment, whereby elasticity of the intermediate zone does not affect the inelasticized transversely opposite side edge zones.

2. The article as set forth by claim 1, wherein each of the first elastic elements comprises
several side segments in each of the inelasticized transversely opposite side edge zones, the side segments being severed from each other and from the intermediate segment.

3. The article as set forth by claim 2, wherein
said chassis comprises a laminate of at least two sheets intermittently bonded together, said first elastic elements being interposed between said two sheets;

a first sheet of said at least two sheets extends continuously in the first waist region from the elasticized intermediate zone into the inelasticized transversely opposite side edge zones and defines the transversely opposite side edge portions of said first waist region;

said fasteners are bonded to said first sheet along the transversely opposite side edge portions of said first waist region; and said first sheet is continuous at locations where the first elastic elements are severed into the respective side segments and intermediate segments.

4. The article as set forth by claim 2, wherein
said chassis comprises a laminate of at least two sheets intermittently bonded together, said first elastic elements being interposed between said two sheets;

a first sheet of said at least two sheets extends continuously in the first waist region from the elasticized intermediate zone into the inelasticized transversely opposite side edge zones and defines the transversely opposite side edge portions of said first waist region;

said fasteners are bonded to said first sheet along the transversely opposite side edge portions of said first waist region; and said chassis further comprises a plurality of slits extending through said first sheet at locations where the first elastic elements are severed into the respective side segments and intermediate segments.

5. The article as set forth by claim 4, wherein said slits extend through said laminate and are arranged in multiple rows elongated in the longitudinal direction.

6. The article as set forth by claim 5, wherein
the transversely opposite side edge portions of said first waist region are permanently bonded to transversely opposite side edge portions of said second waist region at a plurality of bonding sites to define said article as a pull-on diaper;

at least one of said rows is located adjacent the bonding sites to define a tear line along which said first waist region is tearable to disconnect the first waist region from the second waist region.

7. The article as set forth by claim 5, further comprising
reinforcing layers attached to the first sheet and covering some of the slits, without covering other slits located transversely outboard of said some slits;

said fasteners being attached to said reinforcing layers in regions above said some slits.

8. The article as set forth by claim 7, wherein
each of said reinforcing layers extends continuously from the elasticized intermediate zone into the respective inelasticized transversely opposite side edge zone of said first waist region.

9. The article as set forth by claim 8, wherein said reinforcing layers consist of hardened adhesive.

* * * * *